United States Patent [19]

Barwich et al.

[11] Patent Number: 5,223,645

[45] Date of Patent: Jun. 29, 1993

[54] UNSATURATED PHENONE DERIVATIVES AND THEIR USE AS CONTACT ADHESIVES

[75] Inventors: Juergen Barwich, Neustadt; Gerd Rehmer, Beindersheim; Kaspar Bott, Mannheim, all of Fed. Rep. of Germany

[73] Assignee: BASF Aktiengesellschaft, Ludwigshafen, Fed. Rep. of Germany

[21] Appl. No.: 764,205

[22] Filed: Sep. 23, 1991

[30] Foreign Application Priority Data

Nov. 22, 1990 [DE] Fed. Rep. of Germany ....... 4037079

[51] Int. Cl.$^5$ .......................................... C07C 233/65
[52] U.S. Cl. .................. 564/158; 564/152; 564/153; 564/170; 564/171; 564/176; 564/177; 564/183; 560/9; 560/19; 560/151; 560/152; 560/155; 560/169; 562/553; 562/561
[58] Field of Search ............... 564/158, 170, 176, 183, 564/152, 177, 171, 153; 568/332; 560/9, 19, 151, 155, 152, 169; 562/553, 561

[56] References Cited

U.S. PATENT DOCUMENTS

| | | | |
|---|---|---|---|
| 3,022,268 | 2/1962 | Armitage et al. | 564/158 |
| 3,135,609 | 6/1964 | Klinger | 564/158 |
| 3,214,492 | 10/1965 | Tocker | 526/316 |
| 3,429,852 | 2/1969 | Skoultchi | 522/220 |
| 4,009,208 | 2/1977 | Lesher | 564/158 |
| 4,063,947 | 12/1977 | Pochan et al. | 430/58 |

FOREIGN PATENT DOCUMENTS

| | | |
|---|---|---|
| 2818763 | 11/1978 | Fed. Rep. of Germany . |
| 3820463 | 12/1989 | Fed. Rep. of Germany . |
| 3820464 | 2/1990 | Fed. Rep. of Germany . |
| 3844445 | 7/1990 | Fed. Rep. of Germany . |
| 3844444 | 8/1990 | Fed. Rep. of Germany . |
| 61-161248A | 7/1986 | Japan ................................. 564/158 |

*Primary Examiner*—Allen J. Robinson
*Assistant Examiner*—Shailendra Kumar
*Attorney, Agent, or Firm*—Oblon, Spivak, McClelland, Maier & Neustadt

[57] ABSTRACT

Unsaturated phenone derivatives of the general formula I

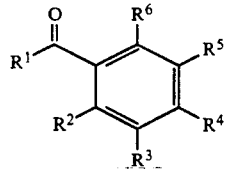

where $R^1$ is $C_1$–$C_4$-alkyl, cyclopropyl, cyclopentyl, cyclohexyl, indanonyl, tetralonyl, phenyl or phenyl in which some or all of the hydrogen atoms have been replaced by a $C_1$–$C_4$-alkyl, $C_1$–$C_4$-alkoxy or $C_1$–$C_4$-thioalkyl group, or together with $R^2$ or $R^6$ forms an ethylene or propylene bridge, $R^2$ to $R^6$ are each hydrogen, $C_1$–$C_4$-alkyl, $C_1$–$C_4$-alkoxy or $C_1$–$C_4$-thioalkyl, and $R^3$, $R^4$ and $R^5$ may each additionally be hydroxyl, $R^2$ or $R^6$ may additionally together with $R^1$ form an ethylene or propylene bridge and one or more, but not more than three, of the radicals $R^2$ to $R^6$ are a group of the general formula II

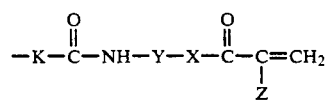

or III

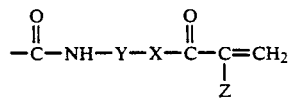

where K is $C_1$–$C_{10}$-alkylene which may contain 1 or 2 oxygen or sulfur atoms, Y is straight-chain or branched $C_1$–$C_{10}$-alkylene or is $C_1$–$C_{10}$-alkylene which is substituted by carboxyl, a carboxylate anion, an alkyl $C_1$–$C_4$-carboxylate group or hydroxyl, X is —NH— or —(N-Alkyl)— of 1 to 4 carbon atoms and Z is hydrogen or $C_1$–$C_4$-alkyl.

2 Claims, No Drawings

UNSATURATED PHENONE DERIVATIVES AND THEIR USE AS CONTACT ADHESIVES

The present invention relates to unsaturated phenone derivatives of the general formula I

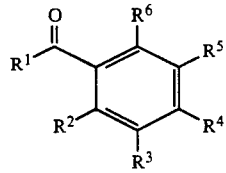

where
$R^1$ is $C_1$–$C_4$-alkyl, cyclopropyl, cyclopentyl, cyclohexyl, indanonyl, tetralonyl, phenyl or phenyl in which some or all of the hydrogen atoms have been replaced by a $C_1$–$C_4$-alkyl, $C_1$–$C_4$-alkoxy or $C_1$–$C_4$-thioalkyl group, or together with $R^2$ or $R^6$ forms an ethylene or propylene bridge, $R^2$ to $R^6$ are each hydrogen, $C_1$–$C_4$-alkyl, $C_1$–$C_4$-alkoxy or $C_1$–$C_4$-thioalkyl, and $R^3$, $R^4$ and $R^5$ may each additionally be hydroxyl, $R^2$ or $R^6$ may additionally together with $R^1$ form an ethylene or propylene bridge and one or more, but not more than three, of the radicals $R^2$ to $R^6$ are a group of the general formula II

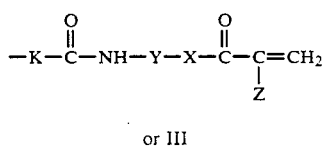

or III

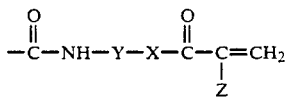

where
K is $C_1$–$C_{10}$-alkylene which may contain 1 or 2 oxygen or sulfur atoms,
Y is straight-chain or branched $C_1$–$C_{10}$-alkylene or is $C_1$–$C_{10}$-alkylene which is substituted by carboxyl, a carboxylate anion, an alkyl $C_1$–$C_4$-carboxylate group or hydroxyl, X is —NH— or —(N-Alkyl)— of 1 to 4 carbon atoms and
Z is hydrogen or $C_1$–$C_4$-alkyl.

The present invention furthermore relates to a process for the preparation of monomers, and polymers which contain the unsaturated phenone derivatives and the use of the polymers as contact adhesives.

Unsaturated phenone derivatives of the general structure

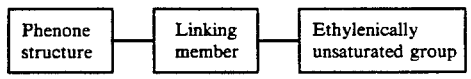

are known. Polymers of these monomers are particularly suitable for use for contact adhesives since they are crosslinkable by exposure to UV light, i.e. have a higher internal strength after exposure. The adhesion to substrates is effected by polar groups.

U.S. Pat. No. 3,214,492 describes compounds of the general formula (VI)

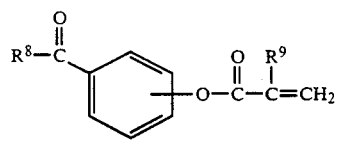

where $R^8$ is —$CH_3$ or —$C_6H_5$ and $R^9$ is —H or —$CH_3$.

Similar acryloxy- or methacryloxy-containing acetophenone or benzophenone derivatives are disclosed in U.S. Pat. No. 3,429,852.

DE-A-28 18 763 relates to compounds of the general formula VII

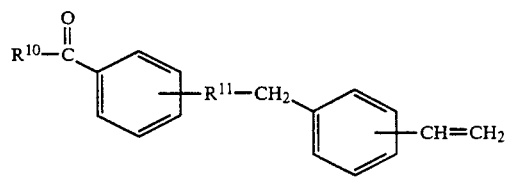

where
$R^{10}$ is —$C_nH_{2n+1}$ in which n is from 1 to 3 or —$C_6H_5$,
$R^{11}$ is —O—,

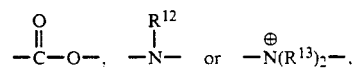

$R^{12}$ is —H or —$C_nH_{2n+1}$ in which n is from 1 to 8 and $R^{13}$ is —$C_nH_{2n+1}$ in which n is from 1 to 4.

DE-A-38 20 464 and DE-A-38 20 463 describes monomers which are obtained by reacting a phenone derivative, which is substituted by hydroxyl in the phenyl nucleus, with an unsaturated isocyanate.

DE-A-38 44 445 and DE-A-38 44 444 disclose monomers which are prepared for reacting a phenone derivative, which is likewise substituted by hydroxyl in the phenyl nucleus, with an unsaturated activated carboxylate.

The unsaturated phenone derivatives should have very high photochemical reactivity, thermal stability and stability to hydrolysis. Furthermore, the polymers which contain the unsaturated phenone derivatives should adhere readily to substrates. That the unsaturated phenone derivatives are obtainable by a very simple preparation process is of particular importance with regard to their availability. Good copolymerization behavior is essential with regard to the use of the unsaturated phenone derivatives in copolymers.

It is an object of the present invention to provide unsaturated phenone derivatives which as far as possible meet all of the abovementioned requirements.

We have found that this object is achieved by unsaturated phenone derivatives as claimed in claim 1.

Particularly suitable unsaturated phenone derivatives of the formula I are those in which $R^1$ is phenyl or $C_1$–$C_4$-alkyl. $R^2$, $R^3$, $R^4$, $R^5$ and $R^6$ are preferably each hydrogen, $C_1$–$C_4$-alkyl or $C_1$–$C_4$-alkoxy, and one or more, but not more than three, of the radicals $R^2$–$R^6$ are a group of the general formula II or III. The unsaturated phenone preferably contains only one group of the general formula II or III, in particular it contains this group as substituent $R^4$. $R^2$, $R^3$, $R^5$ and $R^6$ are particularly preferably hydrogen.

In the general formula II or III, K is preferably $C_1$–$C_6$-alkylene or $C_1$–$C_6$-alkylene containing 1 or 2 oxygen atoms. K is particularly preferably $C_1$–$C_4$-alkylene or $C_1$–$C_4$-oxyalkylene in which the oxygen atom is bonded directly to the phenyl ring.

Y is preferably (straight-chain or branched) $C_1$–$C_6$-alkylene or $C_1$–$C_6$-alkylene which is substituted by carboxyl, a carboxylate anion, an alkyl $C_1$–$C_4$-carboxylate group or hydroxyl. Y is particularly preferably $C_1$–$C_4$-alkylene which may be substituted by one or two carboxyl groups or carboxylate anions.

X is preferably —NH—, —(N—CH$_3$)— or —(-N—CH$_2$—CH$_3$)— and Z is preferably hydrogen or methyl.

The novel phenones are obtainable by the novel process in a simple manner by reacting a compound having a nitrile functional group of the general formula IV

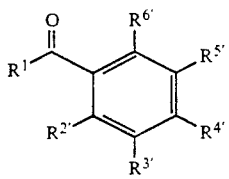

with a compound of the general formula V

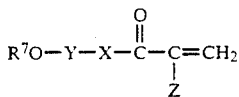

where $R^1$ has the abovementioned meanings, $R^7$ is hydrogen or $C_1$–$C_4$-alkyl and $R^{2'}$ to $R^{6'}$ are each hydrogen, $C_1$–$C_4$-alkyl, $C_1$–$C_4$-alkoxy or $C_1$–$C_4$-thioalkyl, and $R^{3'}$, $R^{4'}$ and $R^{5'}$ may additionally be hydroxyl, $R^{2'}$ and $R^{6'}$ together with $R^1$ may additionally form an ethylene or propylene bridge and one or more, but not more than three, of the radicals $R^{2'}$ to $R^{6'}$ are a radical —C≡N or —K—C≡N, and K, X, Y and Z have the meanings stated in claim 1.

The reaction takes place in accordance with the following simple reaction scheme, illustrated, for example, for the case where $R^{4'}$ is —K—C≡N or C≡N.

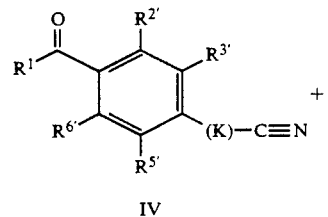

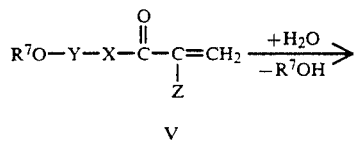

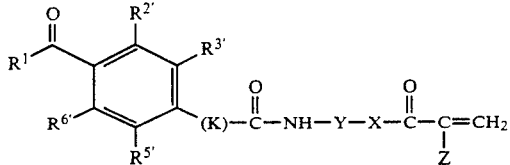

The reaction is preferably carried out in a mixture of sulfuric acid and acetic acid at room temperature. To prevent premature polymerization, in a preferred embodiment a polymerization inhibitor, e.g. nitrobenzene, quinone, hydroquinone monomethyl ether, 2,6-di-tert-butyl-p-cresol, phenothiazine or a Cu(II) salt, such as CuSO$_4$ or CuCl$_2$, is added.

Polymerization can also be inhibited by the presence of atmospheric oxygen.

The compound V is preferably used in excess, for example in a 5–15% molar excess, based on compound IV.

The reaction time is in general from 1 to 10, in particular from 2 to 4, hours.

The reaction solution is preferably worked up by adding water or ice to the reaction product, filtering off the reaction product and recrystallizing it from a polar protic solvent, e.g. ethanol.

Conversion of carboxyl groups present in the compound into salts, for example potassium or sodium carboxylates, can be effected, for example, by adding the corresponding alkali metal hydroxides.

The starting compounds are compounds known per se.

Nitriles of the general formula IV can be obtained by known processes, either by nucleophilic substitution of halogens of corresponding halogenated phenone derivatives by the cyanide group or by reacting α-chloroacetonitrile or γ-chlorobutyronitrile with the potassium salt of the corresponding hydroxybenzophenone.

The preparation of compounds of the formula V, for example N-(hydroxymethyl)-methacrylamide, is described in H. Feuer and U. E. Lynch, J. Am. Chem. Soc. 75 (1953), 5027 or in U.S. Pat. No. 3,064,050. N-(Hydroxymethyl)methacrylamide is accordingly obtainable by reacting methacrylamide with paraformaldehyde in anhydrous carbon tetrachloride.

N-(Hydroxymethyl) acrylamide is obtainable, for example, by an analogous reaction in anhydrous ethylene chloride.

Furthermore, unsaturated carboxamido-N-methyl alkyl ethers are obtainable, for example, according to E. Müller, K. Dinges and W. Graulich, Makromol. Chem. 57 (1962), 27, by the action of alkanols in the corresponding methylol compound.

The novel, unsaturated phenone derivatives have, as a rule, completely satisfactory crystallization behavior and are usually solid at room temperature, so that they are readily obtainable in high purity by recrystallization. They are particularly suitable as copolymerizable monomers for the preparation of polymers which have high internal strength after exposure to actinic radiation. However, they can also be polymerized with themselves. Remarkably, they have high photochemical reactivity, particularly in the short-wavelength to relatively long-wavelength UV range from 250 to 400 nm.

When the novel phenones are used for the preparation of homo- and copolymers, the usual processes of vinyl polymerization can be employed. For example, such polymers can be obtained by free radical mass, suspension, solution or emulsion polymerization. The polymerization of the unsaturated phenones can, however, also be effected by ionic catalysts or by stereospecific catalysts of the Ziegler type.

The polymerization is preferably initiated by free radicals. The bond between the phenone structure and the skeleton of the polymers has high thermal stability, with the result that the polymers can be satisfactorily processed even at elevated temperatures. The phenones are particularly suitable for free radical aqueous emulsion polymerization processes.

Particularly suitable comonomers for the novel phenone derivatives are, for example, styrene, α-methylstyrene, acrylates and methacrylates of alkanols of 1 to 24 carbon atoms, such as methyl acrylate, methyl methacrylate, ethyl acrylate, ethyl methacrylate, n-propyl acrylate, n-propyl methacrylate, n-, tert- and isobutyl acrylate and methacrylate, 2-ethylhexyl acrylate and methacrylate, isoamyl acrylate, n-heptyl acrylate, isooctyl acrylate, isobornyl methacrylate and isobornyl acrylate, as well as vinyl esters of aliphatic carboxylic acids of 2 to 18 carbon atoms, e.g. vinyl acetate or vinyl propionate, and acrylamide, methacrylamide, N-vinylpyrrolidone, vinylimidazole, N-vinylformamide, N-vinylcaprolactam, acrylic acid, methacrylic acid, acrylonitrile, methacrylonitrile, maleic anhydride, itaconic anhydride, maleic acid and fumaric acid, diesters, diamides and imides of olefinically unsaturated dicarboxylic acids, e.g. maleimide, dimethyl maleate, dimethyl fumarate, di-n-butyl maleate or di-n-butyl fumarate, and the half esters and semiamides of olefinically unsaturated dicarboxylic acids, such as mono-n-butyl maleate and mono-n-butylmaleamide, as well as monomers such as vinyl chloride, vinylidene chloride, vinyl fluoride, ethene, propene, butadiene, diallyl phthalate and isoprene, and mixtures of the stated monomers. Monoethylenically unsaturated compounds are preferably used as comonomers.

The novel phenones are in general sufficiently soluble in the stated comonomers under the copolymerization conditions. Where carboxyl-containing or carboxylate-containing phenones are used, partial dissolution either in monomers which are likewise very polar, for example methyl acrylate or acrylic acid, or in small amounts of very polar solvents is advisable.

Phenones are also particularly suitable for the preparation of graft copolymers, the phenone being polymerized in the presence of previously prepared vinyl polymers, such as polyvinyl halides or polyvinyl esters or other polymers, such as polyolefins.

Regardless of the polymerization process by which the polymers containing the phenones as copolymerized units are prepared, said polymers all exhibit sensitivity to actinic radiation, in particular in the wavelength range from 250 to 400 nm, and have high internal strength after exposure to said radiation. This high internal strength is evident, for example, from great rigidity, a high melting point and reduced solubility of the polymer in a very wide range of solvents and a resulting greater stability to oils, fats, water and the like. These properties are desirable for many applications, for example when the polymers are used in photoreproduction processes. However, these properties are also advantageous when such polymers are used for coating or impregnation. The phenone-containing polymer is usually not exposed to actinic radiation until it has been shaped into a film, a coating or another article.

Polymers or copolymers of the novel phenones are particularly suitable for use as contact adhesives since they are crosslinkable as a result of exposure to high energy radiation and thus have high internal strength and good adhesion to substrate surfaces. Furthermore, they have high peel strength after exposure to radiation. The weight of the phenones in the copolymers when they are used as contact adhesives is in general from 0.01 to 50, preferably from 0.1 to 10%, by weight, based on the copolymer. For use as contact adhesives, the copolymers are particularly preferably composed of:

a) from 0.25 to 5% by weight of one or more novel phenones and b) from 95 to 99.75% by weight of one or more copolymerizable monoethylenically unsaturated monomers.

Of particular interest for contact adhesives are copolymers whose monomer composition is such that a polymer composed only of the monomers b) would have a glass transition temperature of −45° to 0° C., particularly preferably from −30° to −10° C. According to Fox (T. G. Fox, Bull. Am. Phys. Soc. (Ser II) 1 [1956], 123), the following is a good approximation for the glass transition temperature of copolymers:

$$\frac{1}{T_g} = \frac{X^1}{T_g^1} + \frac{X^2}{T_g^2} + \ldots \frac{X^s}{T_g^s}$$

where $X^1, X^2, \ldots, X^s$ are the mass fractions of the monomers $1, 2, \ldots, s$ and $T_g^1, T_g^2, \ldots T_g^s$ are the glass transition temperatures in degrees Kelvin, of the particular polymers composed only of one of the monomers 1, 2, . . . or s. The glass transition temperatures of the abovementioned monomers b) are essentially known and are listed in, for example, J. Brandrup and E. H. Immergut, Polymer Handbook 1st Ed. J. Wiley, New York 1966 and 2nd Ed. J. Wiley, New York 1975.

The polymers and copolymers which are suitable as a contact adhesive preferably have a glass transition temperature of from −45° to 0° C., in particular from −30° to −10° C.

In addition, such polymers which are suitable as contact adhesives preferably have, before their exposure in tetrahydrofuran (THF) at 25° C., a K value of from 20 to 70, particularly preferably from 30 to 55 (1% strength by weight solution in THF).

The K value is a relative viscosity number which is determined according to DIN 53,726. It characterizes the mean molecular weight of the polymer. The initial surface tack of the contact adhesives described can be modified by adding not more than 50% by weight of tackifiers, such as coumarone/indene, alkylphenol/formaldehyde or alkyd resins to the novel polymers. Minor amounts, preferably not more than 30, in particular not more than 15%, by weight of mineral fillers, plasticizers, polychlorinated hydrocarbons and liquid paraffins may also be added to the novel polymers suitable as contact adhesives, before they are used.

The novel contact adhesives are preferably used for the production of self-adhesive articles, in particular for the production of self-adhesive tapes and films, which very generally consist of a substrate and a contact adhesive. Depending on the application, the substrates are selected from a wide range. Suitable substrates include textile fabrics, papers, plastic films of polyvinyl chloride, polyesters, such as polyethylene glycol terephthalate, cellulose acetate or polypropylene, metal foils of aluminum, copper or lead, as well as foams of polyurethane, polyvinyl chloride, polyethylene and polychloroprene. The novel contact adhesives are preferably applied before exposure to high energy light. Application may be effected from organic solution, preferably having a solids content of from. 50 to 80% by weight, or from the melt and, where organic solutions of the novel polymers are used, the solvent is expelled, in general by means of heat, after coating of the substrate surface. Application is preferably effected from the melt at from 80°0 to 140° C., and may be carried out, for example, by spreading, spraying, roller coating, knife coating or pouring. Because of the polar spacer chain which links the phenone structure to the polymer skeleton, the contact adhesives described above exhibit particular adhesion to polar substrates.

Exposure to high energy, preferably ultraviolet, light can be effected directly after application, after removal of the solvent (application from the solution) or after passage through a heating zone, thermostated zone and/or cooling zone (in particular for application from the melt). Commercial UV lamps, which preferably emit radiation in a wavelength range of from 250 to 400 nm, can be used for exposure. For example, medium pressure mercury lamps having a radiant power of from 80 to 120 W/cm, as described in, for example, Sources and Applications of Ultraviolet Radiation, R. Philips, Academic Press, London 1983, are suitable. The exposure time depends on the thickness of the coating, the UV emission spectrum and the radiant power of the radiation source used and on the particular phenones I present as copolymerized units. However, it can readily be determined in preliminary experiments. The presence of an inert gas is not required during exposure.

EXAMPLES

EXAMPLE 1

Preparation of novel phenones

For the phenones prepared, the structure and composition were determined by $^1$H-NMR, $^{13}$C-NMR, IR and mass spectroscopy and elemental analysis.

a) N-(Acrylamidomethyl)-benzophenone-4-carboxamide

A mixture of 132 g of sulfuric acid, 68 g of acetic acid, 0.10 mol of 4-cyanobenzophenone, 0.11 mol of N-methylolacrylamide and 100 ppm of 2,6-di-tert-butyl-p-cresol were stirred for 4 hours at room temperature. The reaction mixture was hydrolyzed by adding ground ice, and the crystalline precipitate formed was filtered off under suction after about 20 hours. The product was washed with water and dried in the air. Recrystallization was carried out from ethanol.

The compounds b) to g) were prepared in a similar manner. Table 1 shows the structural formulae and Table 2 the analytical data.

TABLE 1

Acid-catalyzed addition reaction of N-methylolacrylamide (= Amol) or α-acrylamidoglycolic acid (= AGA) with nitriles

| Compound | Structural formulae | Starting materials |
|---|---|---|
| (a) | Benzophenone-C(=O)-NH-CH₂-NH-C(=O)-CH=CH₂ | Benzophenone-CN and Amol |
| (b) | Benzophenone-CH₂-C(=O)-NH-CH₂-NH-C(=O)-CH=CH₂ | Benzophenone-CH₂-CN and Amol |
| (c) | CH₃-C(=O)-C₆H₄-C(=O)-NH-CH₂-NH-C(=O)-CH=CH₂ | NC-C₆H₄-C(=O)-CH₃ and Amol |
| (d) | Benzophenone-OCH₂-C(=O)-NH-CH₂-NH-C(=O)-CH=CH₂ | Benzophenone-OCH₂-CN and Amol |
| (e) | Benzophenone-O(CH₂)₃-C(=O)-NH-CH₂-NH-C(=O)-CH=CH₂ | Benzophenone-O(CH₂)₃-CN and Amol |

TABLE 1-continued

Acid-catalyzed addition reaction of N-methylolacrylamide
(= Amol) or α-acrylamidoglycolic acid (= AGA) with nitriles

| Compound | Structural formulae | Starting materials |
|---|---|---|
| (f) | ![benzophenone]–OCH$_2$–C(=O)–NH–CH(CO$_2$H)–NH–C(=O)–CH=CH$_2$ | ![benzophenone]–OCH$_2$–CN and AGA |
| (g) | ![benzophenone]–O(CH$_2$)$_3$–C(=O)–NH–CH(CO$_2$H)–NH–C(=O)–CH=CH$_2$ | ![benzophenone]–O(CH$_2$)$_3$–CN and AGA |

TABLE 2

| Com. pound | Yield | Recrystallization from | Melting point | Elemental analysis | C | H | O | N |
|---|---|---|---|---|---|---|---|---|
| (a) | 85% | Ethanol | 183–186° C. | Calc. | 70.12 | 5.23 | 15.57 | 9.09 |
| | | | | Found | 70.1 | 5.2 | 15.9 | 8.8 |
| (b) | 77.5% | Ethanol | 193–196° C. | Calc. | 70.79 | 5.63 | — | 8.69 |
| | | | | Found | 70.5 | 5.8 | — | 8.3 |
| (c) | 86% | Dimethyl-formamide/water (1:2) | 197–201° C. | Calc. | 63.40 | 5.73 | 19.49 | 11.38 |
| | | | | Found | 62.9 | 5.9 | 19.7 | 11.1 |
| (d) | 99% | Ethanol | 176–178° C. | Calc. | 67.45 | 5.36 | 18.91 | 8.28 |
| | | | | Found | 67.0 | 5.5 | 19.3 | 8.1 |
| (e) | 93% | Ethanol | 140° C. (polymerization) | Calc. | 68.84 | 6.05 | — | 7.65 |
| | | | | Found | 68.4 | 6.2 | — | 7.5 |
| (f) | 88% | Aceto-nitrile | 192–194° C. | Calc. | 62.82 | 4.75 | 25.10 | 7.33 |
| | | | | Found | 62.6 | 4.9 | 25.3 | 7.2 |
| (g) | 91% | Purification by precipitation from the aqueous Na salt solution with HCl | 187–191° C. | Calc. | 64.38 | 5.40 | — | 6.83 |
| | | | | Found | 64.2 | 5.6 | — | 6.9 |

EXAMPLE 2

Preparation of a copolymer 50 g of a monomer mixture of
500 g of n-butyl acrylate,
290 g of 2-ethylhexyl acrylate,
185 g of methyl acrylate
25 g of acrylic acid and
6.5 g of N-(acrylamidomethyl)-benzophenone-4-carboxamide
in 150 g of toluene were heated to a reaction temperature of 80° C. in the presence of 1 g of tert-butyl peroctoate (polymerization initiator). Thereafter, the remainder of the monomer mixture was added at this temperature in the course of 5 hours and, simultaneously with this, a solution of 19 g of tert-butyl peroctoate in 100 g of toluene was added in the course of 3 hours. Polymerization was then continued at 120° C. and the solvent was finally separated off by distillation.

A polymer which was free-flowing at room temperature and had a K value of 44 in THF (25° C.) was obtained.

EXAMPLE 3

Testing the contact adhesive properties of the polymer from Example 2.
a) Preparation of the test strips For the preparation of the test strips, the polymer was applied from the melt in a layer thickness of 25 g/m² to a polyester film as a substrate.

The polyester film was then passed at a speed of 20 m/min and at a distance of 10 cm below two medium pressure mercury lamps (80 W/cm) arranged in series (11 cm apart). Strips 2 cm wide and 5 cm long were cut from the self-adhesive film thus obtained.

b) Testing the shear strength

The test strips were applied over a length of 2.5 cm to a chromium-plated stainless steel sheet (V2A) using a weight of 2.5 kg in such a way that they projected on one side and the opposite side was not coated. The steel sheet was then stored for 24 hours at 20° C. and atmospheric pressure. That end of the steel sheet which was not adhesively bonded was then fastened between two clamping jaws and the opposite projecting self-adhesive tape, suspended freely, was loaded with a weight of 2 kg at 25° C. and with a weight of 1 kg at 50° C. The time taken to break the adhesive film is a measure of the shear strength. For comparison, the test was repeated with polyester films which had not been exposed to radiation. The results are shown in Table 3.

c) Testing the peel strength

To determine the peel strength of the test strips on the surface of a substrate, said strips were rolled onto a chromium-plated stainless steel sheet (V2A) over a length of 2.5 cm using a weight of 2.5 kg. 24 hours thereafter (storage at 20° C. and atmospheric pressure), the force required to peel off the test strips backward at a peeling angle of 180° C. and a speed of 300 mm/min in a tensile test apparatus was determined. The results are likewise shown in Table 3.

TABLE 3

|  | Shear strength [h] | | Peel strength [N/cm] |
| --- | --- | --- | --- |
|  | 25° C. | 50° C. |  |
| with exposure to radiation | >24 | >24 | 4.3 |
| without exposure to radiation | <1 | <1 | — |

We claim:

1. An unsaturated phenone derivative of the formula I

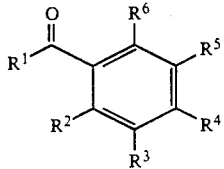

where

R$^1$ is C$_1$-C$_4$-alkyl, cyclopropyl, cyclopentyl, cyclohexyl, indanonyl, tetralonyl, phenyl or phenyl in which some or all of the hydrogen atoms have been replaced by a C$_1$-C$_4$-alkyl, C$_1$-C$_4$-alkoxy or C$_1$-C$_4$-thioalkyl group, or together with R$^2$ or R$^6$ forms an ethylene or propylene bridge, R$^2$ to R$^6$ are each hydrogen, C$_1$-C$_4$-alkyl, C$_1$-C$_4$-alkoxy or C$_1$-C$_4$-thioalkyl, and R$^3$, R$^4$, and R$^5$ may each additionally be hydroxyl, R$^2$ or R$^6$ may additionally together with R$^1$ form an ethylene or propylene bridge with the proviso that at least 1, but not more than 3, of the radicals R$^2$ to R$^6$ are a group of the formula II

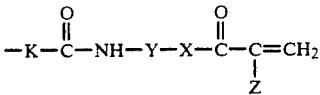

or III

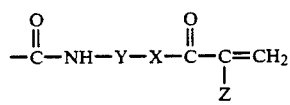

where

K is C$_1$-C$_{10}$-alkylene which may contain 1 or 2 oxygen or sulfur atoms,

Y is a straight-chain or branched C$_1$-C$_{10}$-alkylene or is C$_1$-C$_{10}$-alkylene which is substituted by carboxyl, a carboxylate anion, an alkyl C$_1$-C$_4$-carboxylate group or hydroxyl, X is —NH— or —(N-alkyl)— of 1 to 4 carbon atoms and Z is hydrogen or C$_1$-C$_4$-alkyl.

2. A phenone derivative as claimed in claim 1, wherein R$^1$ is phenyl or C$_1$-C$_4$-alkyl, R$^2$, R$^3$, R$^5$ and R$^6$ are each hydrogen and R$^4$ is a group of the formula II or III, where K is C$_1$-C$_4$-alkylene or C$_1$-C$_4$-oxyalkylene in which the oxygen atom is bonded directly to the phenyl ring, Y is C$_1$-C$_4$-alkylene which may be substituted by one or two carboxyl groups, carboxylate anions, alkyl C$_1$-C$_4$-carboxylate groups or hydroxyl groups, X is —NH—, —(N—CH$_3$)— or —(N—CH$_2$—CH$_3$)— and Z is hydrogen or methyl.

* * * * *